(12) United States Patent
Elliot et al.

(10) Patent No.: US 11,291,427 B2
(45) Date of Patent: Apr. 5, 2022

(54) ACOUSTIC ANALYZATION OF BONE QUALITY DURING ORTHOPEDIC SURGERY

(71) Applicant: THINK SURGICAL, INC., Fremont, CA (US)

(72) Inventors: Gibson Elliot, Fremont, CA (US); Micah Forstein, Fremont, MI (US)

(73) Assignee: Think Surgical, Inc., Fremont, CA (US)

(*) Notice: Subject to any disclaimer, the term of this patent is extended or adjusted under 35 U.S.C. 154(b) by 266 days.

(21) Appl. No.: 16/430,746

(22) Filed: Jun. 4, 2019

(65) Prior Publication Data
US 2019/0365346 A1 Dec. 5, 2019

Related U.S. Application Data

(60) Provisional application No. 62/680,407, filed on Jun. 4, 2018.

(51) Int. Cl.
| | |
|---|---|
| A61F 2/46 | (2006.01) |
| A61B 8/08 | (2006.01) |
| A61B 5/00 | (2006.01) |
| A61B 34/10 | (2016.01) |
| A61B 6/00 | (2006.01) |
| A61F 2/30 | (2006.01) |
| A61B 17/16 | (2006.01) |
| A61B 17/00 | (2006.01) |

(52) U.S. Cl.
CPC .......... *A61B 8/0875* (2013.01); *A61B 5/7246* (2013.01); *A61B 6/505* (2013.01); *A61B 34/10* (2016.02); *A61F 2/4603* (2013.01); *A61B 5/4509* (2013.01); *A61B 17/16* (2013.01); *A61B 2017/00022* (2013.01); *A61B 2034/108* (2016.02); *A61B 2505/05* (2013.01); *A61F 2002/30736* (2013.01)

(58) Field of Classification Search
CPC combination set(s) only.
See application file for complete search history.

(56) References Cited

U.S. PATENT DOCUMENTS

2003/0023167 A1* 1/2003 Azzam ................ A61B 8/0875
600/449

* cited by examiner

*Primary Examiner* — Sameh R Boles
(74) *Attorney, Agent, or Firm* — Blue Filament Law PLLC (57) ABSTRACT

A method of analyzing the quality of bone at one or more bone regions during an orthopedic surgical procedure includes an initial audio sample being recorded with an acoustic sensor, while a cutting instrument cuts a first region of a bone. The first audio sample is stored as a reference sample that represents a good degree of bone quality. A second audio sample is recorded with the acoustic sensor, while the cutting instrument cuts a second region of the bone. The second audio sample is compared to the reference sample to analyze the bone quality at the second region of the bone. A system for performing the method is also provided.

11 Claims, 7 Drawing Sheets

ACOUSTIC ANALYZATION OF BONE QUALITY DURING ORTHOPEDIC SURGERY

RELATED APPLICATIONS

This application claims priority benefit of U.S. Provisional Application Ser. No. 62/680,407 filed Jun. 4, 2018; the contents of which are hereby incorporated by reference.

TECHNICAL FIELD

The present invention generally relates to the field of computer-assisted orthopedic surgery, and more particularly to the acoustic analysis of bone quality during orthopedic surgery.

BACKGROUND

Throughout a lifetime, bones and joints become damaged and worn through normal use, disease, and traumatic events. Arthritis is a leading cause of joint damage, which can cause cartilage degradation, pain, swelling, stiffness, and bone loss overtime. If the pain associated with the dysfunctional joint is not alleviated by less-invasive therapies, the joint may need to be replaced with a procedure called total joint arthroplasty (TJR). TJR is an orthopedic surgical procedure in which the typically worn articular surfaces of the joint are replaced with prosthetic components, or implants. TJR typically requires the removal of the articular cartilage of the joint including a varying amount of bone. This cartilage and bone is then replaced with synthetic implants, typically metal and plastic, which form the new synthetic joint surfaces.

The accurate placement and alignment of the implants on the bone is a large factor in determining the success of a TJR procedure. A slight misalignment may result in poor wear characteristics, reduced functionality, poor clinical outcomes, and decreased longevity. Therefore, several TJR procedures are now performed with computer-assistance, and even more advanced procedures utilize robotic surgical systems. One such robotic surgical system is the TSOLUTION ONE® Surgical System (THINK Surgical, Inc., Fremont, Calif.), which aids in the planning and execution of total hip arthroplasty (THA) and total knee arthroplasty (TKA). The TSOLUTION ONE® Surgical System includes: a pre-operative planning software program to generate a surgical plan using an image data set and/or 3-D models of the patient's bone and computer-aided design (CAD) models of several implants; and an autonomous surgical robot that precisely mills the bone to receive an implant according to the surgical plan.

Figure 1:
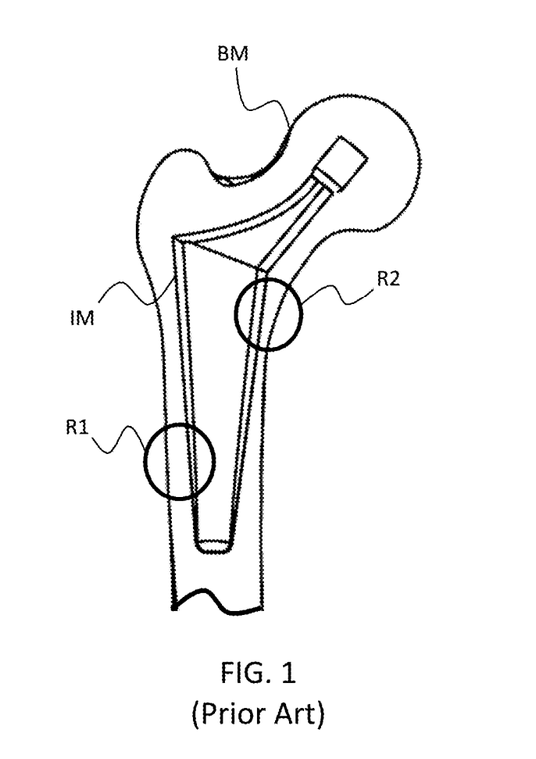
FIG. 1 depicts a prior art bone model having an implant model positioned therein.

With regard to pre-operative planning, prior art FIG. 1 depicts a bone model BM having an implant model IM positioned therein. The user may adjust the model, size, and position of the implant model IM to designate the best fit, fill, and position for the implant. During planning, the user may further adjust the model, size, and/or position of the implant model IM based on the quality of the bone (i.e., bone quality) at one or more bone regions. Bone quality data may be captured using an imaging modality (e.g., computed tomography (CT) dual-energy x-ray (DEXA)) and provided to the user in the form of a value, color, hue, or other indicia (e.g., Hounsfield units). The user may therefore identify bone regions having superior bone quality to aid in planning. For example, the user may identify a first bone region R1 and a second bone region R2 having superior bone quality compared to their neighboring regions and therefore adjust the position of the implant to utilize the superior bone quality. This may improve the longevity of the implant, reduce stress-shielding effects, improve initial implant stability, improve osseointegration, and reduce the occurrence of subsidence and revision.

However, the actual bone quality at those regions (e.g., first bone region 10, second bone region 12) may not coincide with the pre-operative bone quality data presented during planning, and there is currently no method to confirm the actual bone quality during the procedure. Otherwise, such information may be useful to permit the surgeon to adjust the plan intra-operatively and improve clinical outcomes.

Thus, there exists a need for a system and method for analyzing the quality of bone at one or more bone regions during an orthopedic surgical procedure.

SUMMARY OF THE INVENTION

A method of analyzing the quality of bone at one or more bone regions during an orthopedic surgical procedure includes an initial audio sample being recorded with an acoustic sensor, while a cutting instrument cuts a first region of a bone. The first audio sample is stored as a reference sample that represents a good degree of bone quality. A second audio sample is recorded with the acoustic sensor, while the cutting instrument cuts a second region of the bone. The second audio sample is compared to the reference sample to analyze the bone quality at the second region of the bone.

A system for performing the method includes a cutting instrument for cutting the bone and an acoustic sensor for sensing audible data. A processor is provided for processing the audible data. Non-transient storage medium is present for storing the audible data. The storage medium stores an initial audio sample recorded while the cutting instrument cuts a first bone region and the processor compares the initial audio sample to a second audio sample recorded while the cutting instrument cuts a second bone region to analyze the bone quality at the second bone region.

A method of analyzing the bone quality of one or more regions of a bone during an orthopedic surgical procedure includes an image data set of a bone being collected and including bone quality data from several regions of the bone. An initial audio sample is recorded with an acoustic sensor, while a cutting instrument cuts a first region of the bone. The initial audio sample is correlated to the bone quality data associated with the first region of the bone. An expected audio sample is predicted at a second region of the bone based on the correlation and the bone quality data associated with the second region of the bone. An actual audio sample is recorded with the acoustic sensor, while the cutting instrument cuts the second region of the bone. The actual audio sample is compared to the expected audio sample to analyze the bone quality at the second region of the bone.

BRIEF DESCRIPTION OF THE DRAWINGS

The present invention is further detailed with respect to the following drawings that are intended to show certain aspects of the present of invention, but should not be construed as limit on the practice of the invention, wherein.

DETAILED DESCRIPTION

The present invention has utility as a system and method for analyzing the quality of bone at one or more bone regions during an orthopedic surgical procedure. The present invention will now be described with reference to the following embodiments. As is apparent by these descriptions, this invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment may be deleted from the embodiment. In addition, numerous variations and additions to the embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations, and variations thereof.

Further, it should be appreciated that although the systems and methods described herein make reference to the proximal femur, the systems and methods may be applied to other bones and joints in the body illustratively including the hip, ankle, elbow, wrist, skull, and spine, as well as revision of initial repair or replacement of any of the aforementioned bones or joints.

It is to be understood that in instances where a range of values are provided that the range is intended to encompass not only the end point values of the range but also intermediate values of the range as explicitly being included within the range and varying by the last significant figure of the range. By way of example, a recited range of from 1 to 4 is intended to include 1-2, 1-3, 2-4, 3-4, and 1-4.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Unless indicated otherwise, explicitly or by context, the following terms are used herein as set forth below.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

As used herein, the term "registration" refers to the determination of the spatial relationship between two or more objects or coordinate systems such as a computer-assist device, a bone, and/or an image data set of a bone. Illustrative methods of registration known in the art are described in U.S. Pat. Nos. 6,033,415, 8,010,177, 8,036,441, and 8,287,522, and U.S. Pat. App. No. 20160338776.

As used herein, the term "real-time" refers to the processing of input data within milliseconds such that calculated values are available within 10 seconds of computational initiation.

Also described herein are 'computer-assisted surgical devices'. A computer assisted surgical device refers to any device/system requiring a computer to aid in a surgical procedure. Examples of a computer-assisted surgical device include a tracking system, tracked passive instruments, active or semi-active hand-held surgical devices and systems, autonomous serial-chain manipulator systems, haptic serial chain manipulator systems, parallel robotic systems, or master-slave robotic systems, as described in U.S. Pat. Nos. 5,086,401; 7,206,626; 8,876,830; 8,961,536; and 9,707,043, and U.S. Pat. Appl. Pub. 2017/258532.

Figure 2:
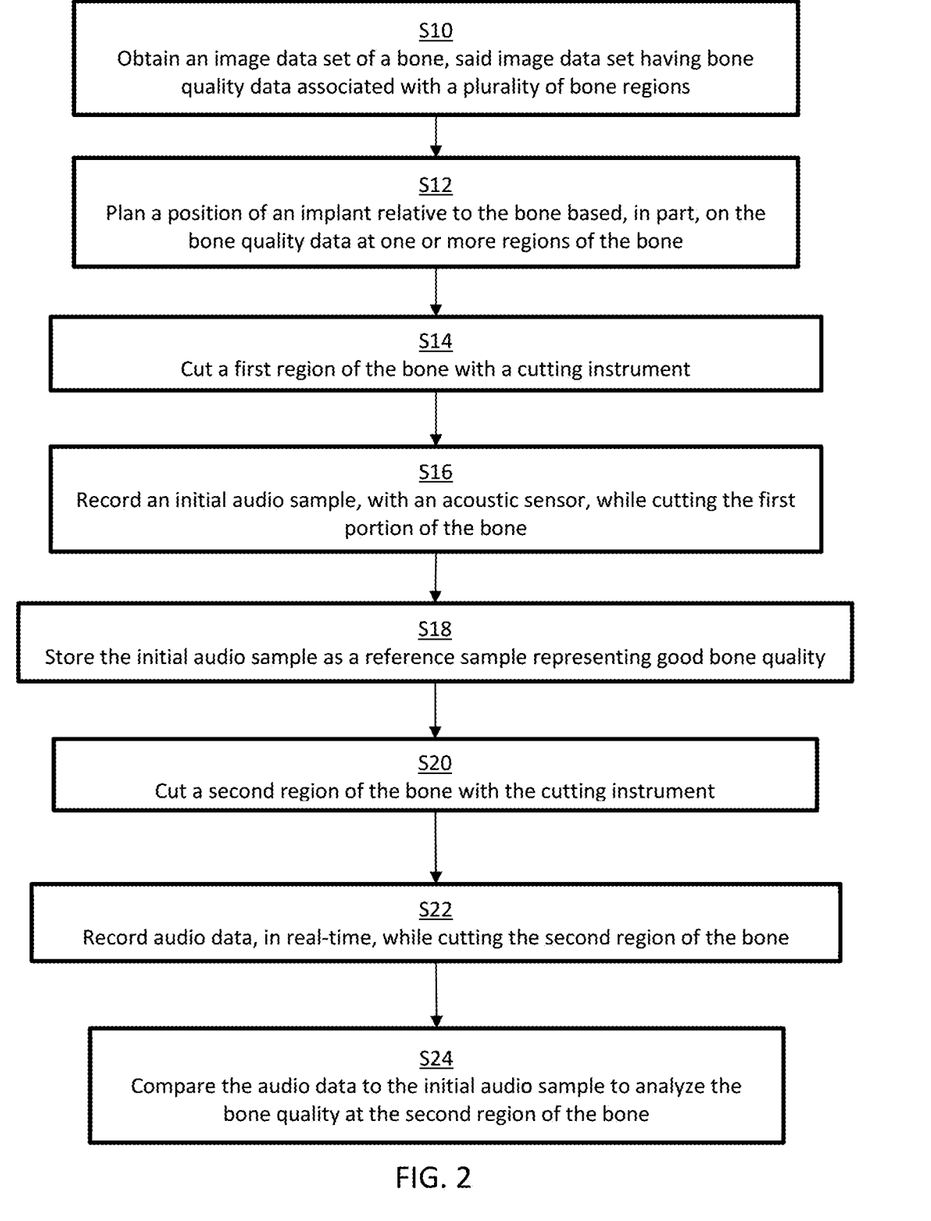
FIG. 2 depicts a method for analyzing bone quality at one or more bone regions in accordance with embodiments of the invention.

With reference now to the drawings, FIG. 2 depicts an embodiment of a method for analyzing the quality of bone at one or more bone regions during orthopedic surgery. An image data set of a patient's bone may be obtained, the image data set having bone quality data associated with a plurality of bone regions (Block S10). A user plans a position for an implant relative to the bone based, in part, on the bone quality data (Block S12). A first region of the bone is cut with a cutting instrument (Block S14) and an initial audio sample is recorded with an acoustic sensor while the first bone region is cut Block S16). The initial audio sample is stored as a reference sample that represents a good degree of bone quality (Block S18). A second region of the bone is cut with the cutting instrument (Block S20) and a second audio sample is recorded while the second bone region is cut (Block S22). The initial audio sample and second audio sample are compared to analyze the quality of the bone at the second bone region (Block S24). Specifics of the method are further described below.

Figure 4:
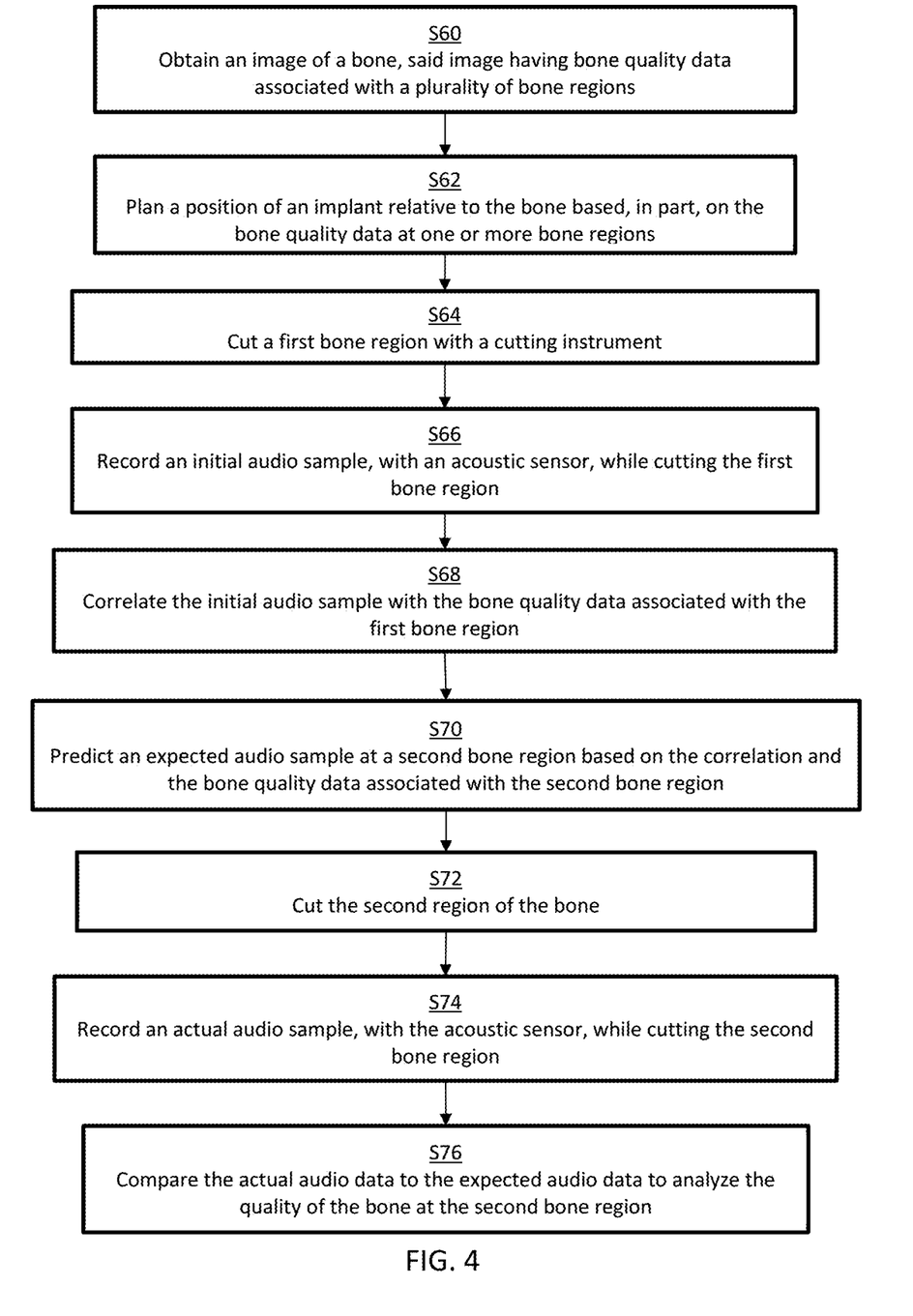
FIG. 4 depicts a method for analyzing bone quality at one or more bone regions in accordance with embodiments of the invention.

The image date set of a patient's bone may be obtained using an imaging modality such as CT, magnetic resonance imaging (MRI), ultrasound, DEXA, X-Ray, or fluoroscopy. The image data set may also be obtained by probing the exposed bone with a tracked device to generate a 3-D point cloud of model of the bone typical of many imageless computer surgical systems (e.g., NavioPFS® manufactured by Smith & Nephew). The image data set includes bone quality data associated with a plurality of bone regions. For example, with reference to FIG. 5, an image slice 30 of a CT scan of the patient's bone is illustratively depicted. The image slice 30 includes an imaged bone 32 and a plurality of values 34 in and around the imaged bone 32. The values 34 indicate the quality of the bone for different regions of the bone. Bone quality may be measured as a function of bone density, architecture, composition, or a combination thereof. The bone quality may also be a relative value with respect to the bone itself, or absolute values relative to a known or standard scale. Further, it should be appreciated that the scale of FIG. 4 is exaggerated for the purpose of illustration and the values 34 may include or be substituted with other indicia including a color scale, color map, gray scale, pixel intensity, or a combination thereof. In a particular embodiment, the bone quality data is provided as Hounsfield units.

In a specific embodiment, the bone quality data is provided as T-Scores and/or Z-scores from DEXA imaging.

Figure 5:
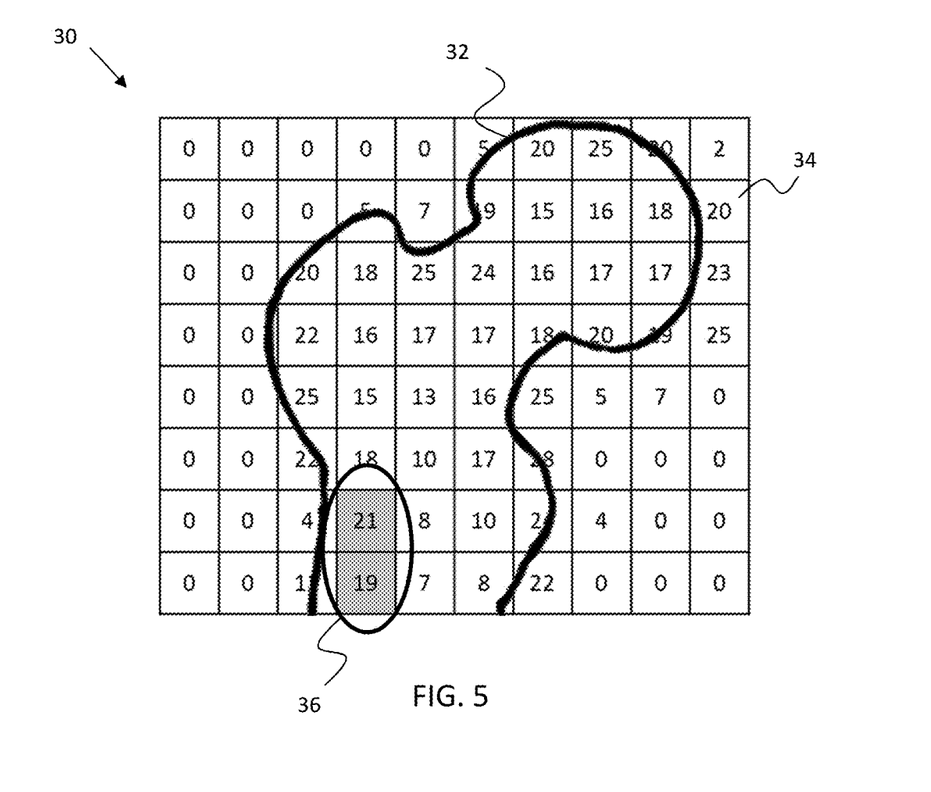
FIG. 5 depicts a slice of a bone image having bone quality data in accordance with embodiments of the invention.

The image data set may be used to aid a user in planning a position for an implant prior to the surgery. The planning may occur in a planning software program. A 3-D model of the patient's bone may be generated from the image data set using methods known in the art. Pre-loaded implant models (e.g., CAD models of the implants) may be readily available to the user. The program includes widgets and other tools that allow the user to position the implant models relative to the 3-D bone model(s). In other embodiments, the user may plan the position for the implant directly on the image date set. In specific embodiments, the user plans the position of the implant based, in part, on the bone quality data. With reference to FIG. 5, the user may identify superior bone quality regions 36 and adjust the position of the implant to exploit these regions. In some embodiments, the locations of the superior bone quality regions 36 are identified and stored with the plan to designate which regions need to be analyzed for bone quality. The final surgical plan is saved and/or transferred to a surgical device to execute the surgical plan.

The surgical device may be a computer-assisted surgical system. The surgical device includes a cutting instrument configured to cut bone. Examples of cutting instruments include an oscillating saw, an end-mill, a cutter, a drill, a chisel, a broach, or a reamer. In a particular embodiment, an initial audio sample is recorded, with an acoustic sensor, while the cutting instrument cuts a first portion of the bone. The first portion of the bone may include the first contact point between the cutting instrument and the bone as determined by the surgical plan. For example, in total hip arthroplasty, the first portion of the bone may be where the cutting instrument first cuts the cortical bone at a proximal portion of the femur (e.g., proximal portion of the greater trochanter, proximal portion of the femoral neck, or the proximal portion of the femoral head). The quality of the cortical bone at these locations is relatively strong and of good quality. Therefore, the initial audio sample recorded while cutting the first region of bone is stored as a reference sample that represents bone having a good degree of bone quality.

Figure 6:
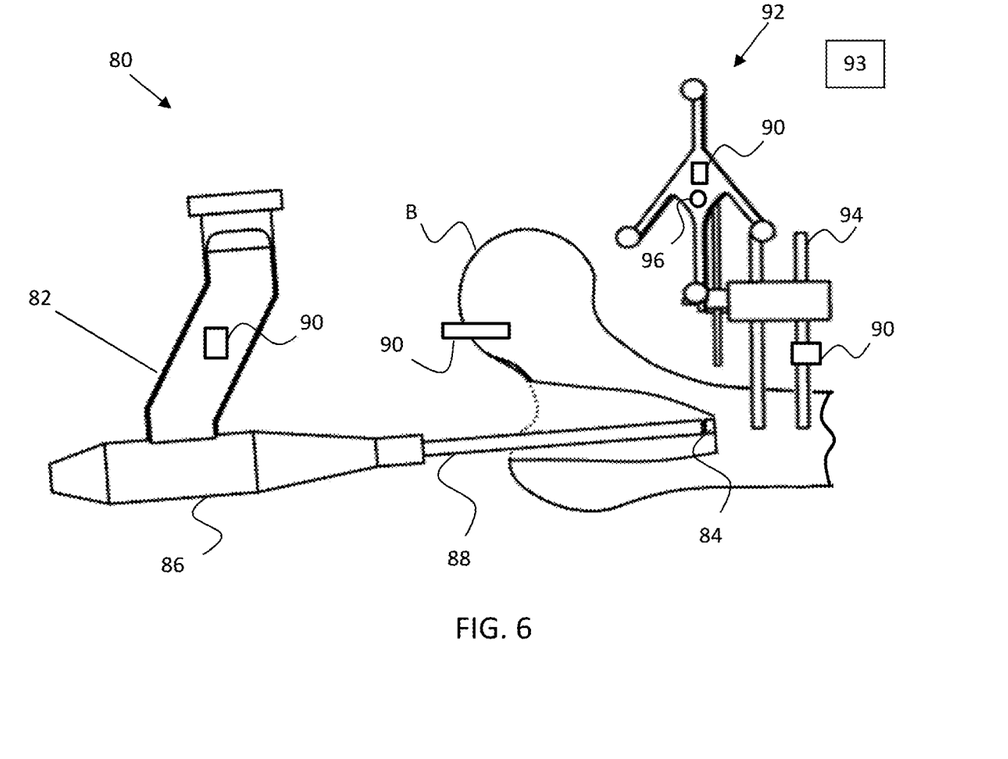
FIG. 6 depicts a system with a cutting instrument cutting bone and one or more acoustic sensors for sensing audible data while cutting the bone in accordance with embodiments of the invention.
Figure 7:
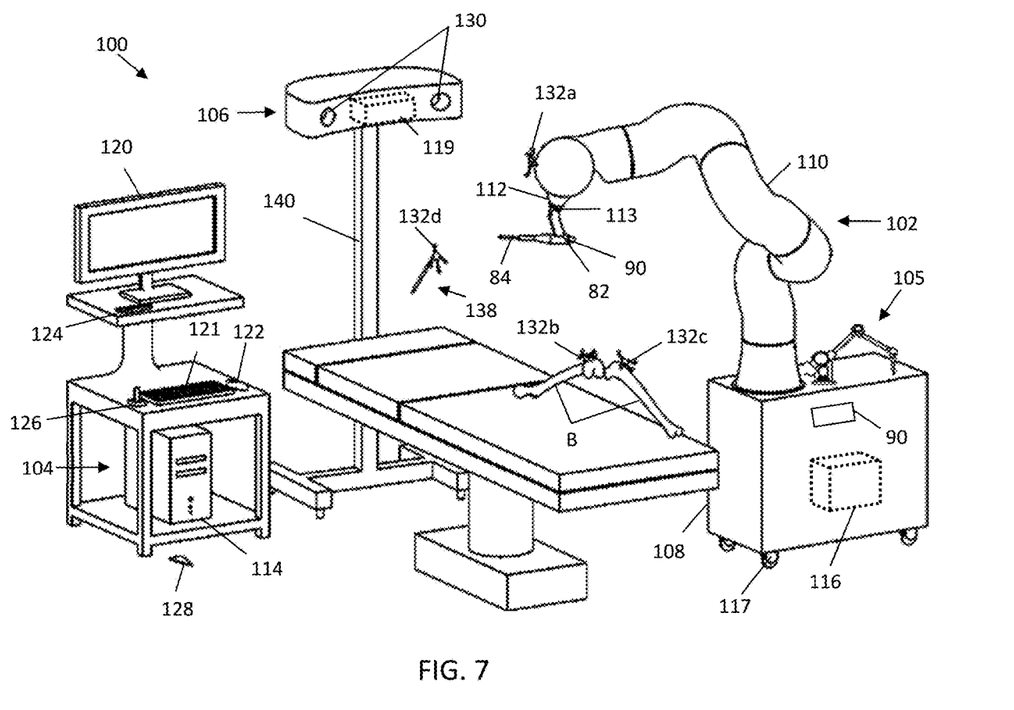
FIG. 7 depicts a robotic surgical system in accordance with embodiments of the invention.

With reference to FIG. 6, an embodiment of a system 80 for recording audio data while cutting portions of a bone B is shown. The system 80 includes an end-effector assembly 82 of a robotic surgical system that operates a cutting instrument 84 for cutting the bone B. The end-effector assembly 82 may include a housing 86 enclosing a motor for rotating the cutting instrument 84. The cutting instrument 84 may include a shaft having a proximal end and a distal end, where the proximal end attaches with the motor and the distal end includes teeth, flutes, edges, or other cutting structures for cutting, milling, grinding or otherwise removing bone. Extending from the housing 86 is a sleeve 88 that surrounds and supports the shaft of the cutting instrument 84. The sleeve 88 may further include internal ball bearings to permit the shaft to rotate therein with minimal friction. The system 80 further includes one or more acoustic sensors 90 (e.g., microphones) for recording audio data. The acoustic sensors 90 may be positioned at various locations about the operating room (OR). For example, an acoustic sensor 90 may be positioned on the end-effector assembly 82, an end-effector of a robotic system more generally, a surgical device, a peripheral to a surgical device, or directly on a cutting instrument. Other suitable locations for the one or more acoustic sensors 90 include a tracking array 92, a bone screw 94, the bone B itself, the walls or ceilings of the operating room, a surgical lamp, a boom pole, a tracking system, the base 108 or arm 110 of a robot 102 (as shown in FIG. 7), and/or on the surgeon or surgeon's gloves, clothing, or personal protective equipment. In some inventive embodiments, the acoustic sensor(s) 90 is an acoustic sensing device. The acoustic sensing device may be a single unit having an acoustic sensor 90 connected to a processor and memory. In other embodiments, the acoustic sensor 110 is read-only and transfers the data, by wire or wireless communication, directly to an external controller, such as a controller controlling a surgical device or robotic system. In a specific embodiment, the tracking array 92 includes an acoustic sensor 90 and a wireless transmitter 96 (e.g., radiofrequency transmitter, Bluetooth, actuating light emitting diode (LED)) for transferring data from the acoustic sensor 90 to an external device. Such data transmission is described in U.S. Pat. App. Pub. No. US2017/0245945 assigned to the assignee of the present application. In any case, the acoustic sensors 90 permit the system 80 or other surgical device or system to record audio data while the cutting instruments cuts bone.

To analyze the bone quality at a second region of the bone B, a second audio sample is recorded while a second region of the bone B is cut. The initial audio sample and second audio sample is then compared for analysis. In a particular embodiment, an audio data software module is used to compares two or more audio samples and transform the audio samples into bone quality data. The software module may transform the audio samples into frequency space using Fourier analysis to compare the audio's frequencies, amplitudes, or harmonics. In specific embodiments, additional inputs are used with the software module illustratively including, the cutting instrument spindle speed, saw oscillating frequency, velocities of a robotic arm or surgical device while making the cuts, force data generated on the cutting instrument, historical data from previous surgical procedures, pre-operative bone quality data from the image data sets, experimental data, and combinations thereof. The additional inputs may be used to normalize the audio samples for better comparison. This process may be repeated to determine the bone quality at other bone regions.

The software module provides output data to the user regarding the analyzed bone quality at the second bone region or any other bone region. The output data may be provided on a display, or provided by other mechanisms including a blinking LED light, an audible signal, a haptic signal, or a combination thereof. The output data may be in the form of a data value or a set of instructions. For example, the output data may be a data value in the form of an absolute bone density value, a relative bone density value, a label (e.g., "good", "bad", "moderate"), or a deviation, difference, or differential mean between the second audio sample and the reference sample. In other embodiments, the output may be a set of instructions, written or graphical, outlining how to adjust the surgical plan if the bone quality at the second bone region is not as expected. In a specific inventive embodiment, the output data and/or instructions may instruct the user to either: a) adjust at least one of a model, a size, or a position of an implant relative to a bone; b) create one or more additional cuts at one or more locations on the bone; c) augment the bone with one or more additional implant components; or d) a combination thereof. Subsequently, the user may adjust at least one of a model, a size, or a position of an implant relative to the bone based on the output data. In another embodiment, the user may subsequently create one or more additional cuts at one or more locations on the bone based on the output data. In a further embodiment, the user may subsequently augment the bone with one more additional implants based on the output data (e.g., placing shims, or wedged components between a primary implant and the bone). Thus, the surgeon can make meaningful adjustments to the plan based on the analyzed bone quality to improve implant longevity, reduce stress-shielding effects, improve initial implant stability, improve osseointegration, and/or reduce the occurrence of subsidence and revision.

It should be appreciated, that the hardware and software components described herein are required to: a) identify the minute similarities/differences between two audio samples; b) transform the audio data into bone quality data; and/or b) normalize audio data as a function of cutting parameters (e.g., cutting velocity, spindle milling speed, cutter geometry); all of which are practically impossible to perform in the human mind alone or with paper and pencil. In addition, these processes and computations are primarily performed in real-time to reduce operating times as rates of infection and surgical complications can increase with surgical operating time.

Figure 3:
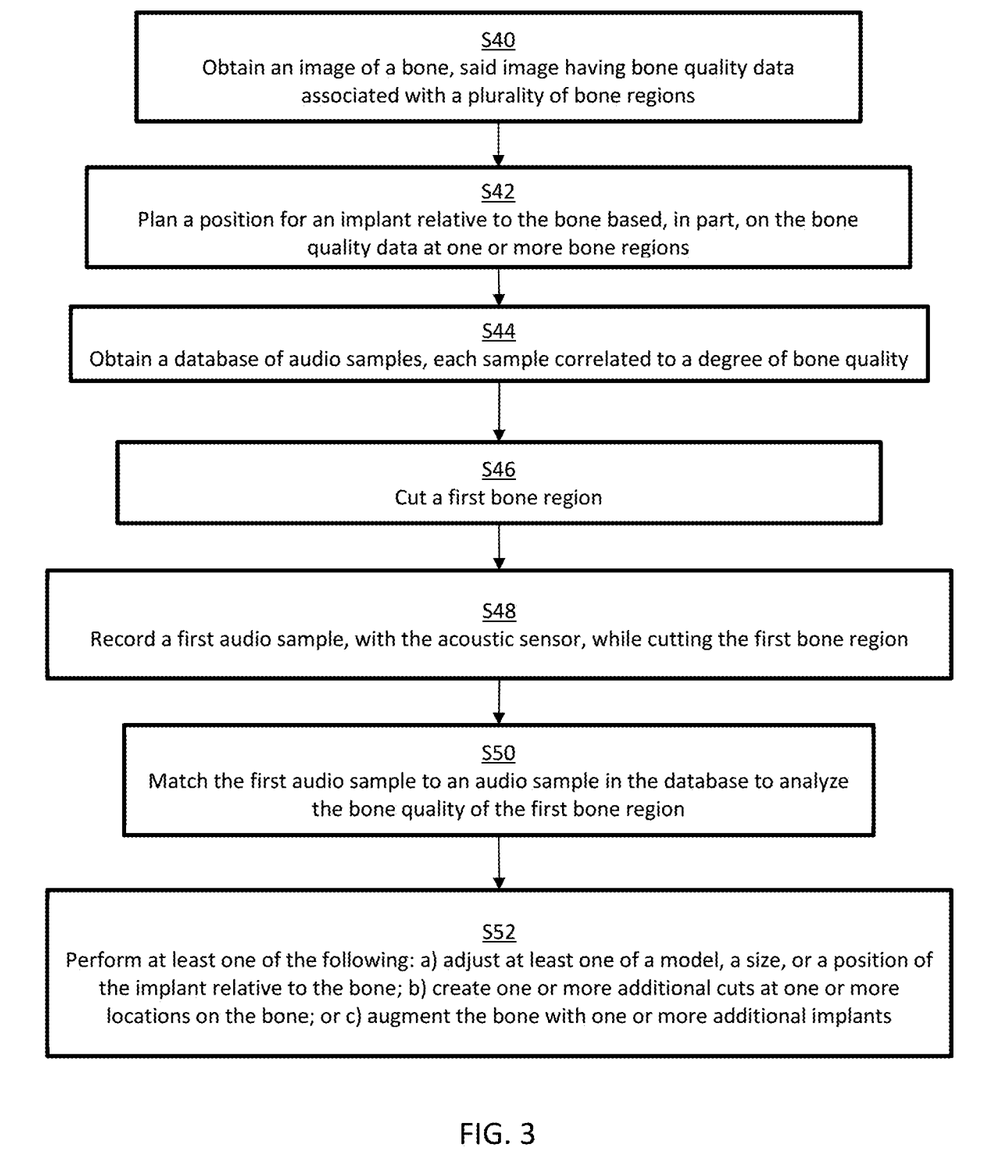
FIG. 3 depicts a method for analyzing bone quality at one or more bone regions in accordance with embodiments of the invention.

With reference to FIG. 3, a particular embodiment of a method for analyzing the quality of bone at one or more bone regions during orthopedic surgery is shown. An image data set of a patient's bone may be obtained, the image data set having bone quality data associated with a plurality of bone regions (Block S40). A user plans a position for an implant relative to the bone based, in part, on the bone quality data (Block S42). A database of audio samples is obtained, where each audio sample in the database is correlated to a degree of bone quality (Block S44). A first region of the bone is cut with a cutting instrument (Block S46) and a first audio sample is recorded with an acoustic sensor while the first region is cut (Block S48). The first audio sample is matched with an audio sample in the database to analyze the bone quality at the first region (Block S50). The cutting, recording, and matching of the audio samples may be repeated for the entire cut and/or for regions specifically specified by the user. Subsequently, data or instructions is provided to the user about the bone quality at the first region and based on the data or instructions the user may perform at least one of the following: a) adjust at least one of a model, a size, or a position of the implant relative to the bone; b) create one or more additional cuts at one or more locations on the bone; c) augment the bone with one or more additional implant components; or d) a combination thereof (Block S52). Specifics of the method are further described below.

Obtaining an image data set of the patient's bone and planning a position for an implant relative to the bone may be performed using the aforementioned techniques. The database of the audio samples may be obtained by several methods. In one embodiment, database may be populated using experimental data. The experimental data may be generated by cutting bone (or substitutes thereof) having a known bone quality and recording audio data while cutting said bone. For example, an audio sample may be recorded while cutting bone having good bone quality. This audio sample is therefore saved in the database representing good bone quality. Other cutting parameters may be stored with each audio sample including the spindle speed, cutting velocity, cutter geometry, and force data. In another embodiment, the database may be populated using historical data. The database may be continuously built based on audio samples recorded from previous patient cases. Then using bone quality data from pre-operative images, the audio samples are correlated to a degree of bone quality, especially where there is correspondence between the bone quality data and audio samples between two or more patients. The database of audio samples may therefore be used to aid in analyzing the bone quality of bone during orthopedic surgery.

More specifically, a first region of the bone is cut and a first audio sample is recorded while cutting the first region of bone as previously described. The first audio sample is then matched to an audio sample in the database to analyze the bone quality at the first region. The first audio sample may be matched by comparing the frequencies, amplitudes, and/or harmonics using techniques as previously described. Other inputs may be matched with a given audio sample as well including the spindle speed, cutting velocity, cutter geometry, and force data to identify the best match. Since a degree of bone quality is correlated to the matched audio sample, the degree of bone quality is therefore known/estimated at the first bone region. This process may be repeated for a plurality of bone regions while cutting the bone. In a particular embodiment, the process is repeated for specific bone regions as identified by the user during surgical planning.

The software module provides output data to the user regarding the analyzed bone quality at the first bone region and any other bone region. The output data may be in the form of data values or a set of instructions as described above. The data or instructions may elicit the user to perform at least one of the following: a) adjust at least one of a model, a size, or a position of the implant relative to the bone; b) create one or more additional cuts at one or more locations on the bone; c) augment the bone with one or more additional implant components; or d) a combination thereof. By implementing said process the surgeon can make meaningful adjustments to improve implant longevity, reduce stress-shielding effects, improve initial implant stability, improve osseointegration, and reduce the occurrence of subsidence and revision.

With reference to FIG. 4, a particular inventive embodiment of a method for analyzing the quality of bone at one or more bone regions during orthopedic surgery is shown. An image data set of a patient's bone is obtained, the image data set having bone quality data associated with a plurality of bone regions (Block S60). The position for an implant is planned relative to the bone based, in part, on the bone quality data at one or more regions (Block S62). A first bone region is cut with a cutting instrument (Block S64) and an initial audio sample is recorded with an acoustic sensor while cutting the first bone region (Block S66). The initial audio sample is correlated with the bone quality data associated with the first bone region (Block S68). An expected audio sample for a second bone region is predicted based on the correlation and the bone quality data associated with the second bone region (Block S70). The second bone region is cut with the cutting instrument (Block S72) and an actual audio sample is recorded while cutting the second bone region (Block S74). The actual audio sample is compared with the expected audio sample to analyze the bone quality at the second bone region (Block S76). Specifics of the method are further described below.

Obtaining the image data set of the patient's bone, planning a position for the implant, cutting the first bone region, and recording the initial audio sample, may all be performed using the aforementioned techniques. The initial audio sample is then correlated to the bone quality data associated with the first bone region from the image data set. For example, the bone quality data at the first bone region may have a particular value, where the correlation equates the initial audio sample to represent that particular value. In some inventive embodiments, a plurality of initial audio samples are collected and correlated to the bone quality data at their corresponding regions. Subsequently, expected audio samples for the remaining bone regions may be predicted using: a) extrapolation, interpolation, or other predictive models; and b) the bone quality data associated with those remaining bone regions. For example, the initial audio sample may have a set of frequencies that represent a bone quality data value of 10. The second bone region may have a bone quality data value of 15, where the predictive model predicts an expected audio sample for the second region based on: a) the initial audio sample representing a bone quality data value of 10; and b) the bone quality data value of 15 at the second bone region. The accuracy of the predictive model clearly increases with more initial audio sample recordings at a plurality of bone regions. In addition, the predictive model may account for other factors including cutting instrument spindle speed, saw oscillating frequency, velocities of a robotic arm or surgical device while making the cuts, force data generated on the cutting instrument, historical data from previous surgical procedures, experimental data, and combinations thereof.

The actual audio sample recorded while cutting the second bone region is compared to the expected audio sample. If the two audio samples are similar then the second bone region is likely consistent with the bone quality data in the image data set and therefore consistent with the surgical plan. Otherwise, the surgeon may adjust the surgical plan with the provided output data from the software module as described above.

Other inventive embodiments of a method for analyzing the quality of bone at one or more bone regions during orthopedic surgery may include the following. The end-effector or cutting instrument may include a force sensor for sensing the forces imposed on the end-effector. The acoustic data may be correlated with the force sensor data while cutting the bone to analyze the bone quality. Experimental or historical data may be used to define the correlation between force data, acoustic data, and bone quality. For example, a set of experiments may be executed while cutting bone, or regions of bone, having known bone qualities. The forces and audio samples are recorded while cutting the bone regions to generate the correlation. Then, while actively cutting the bone, the inputs of the force data and audio data result in an output of bone quality data in real-time. As before, the surgeon may make various adjustments to the surgical plan based on the bone quality data.

Surgical System

With reference to FIG. 7, an example of a computer-assisted surgical system 100 in the context of an operating room (OR) is shown. The surgical system 100 generally includes a surgical robot 102, a computing system 104, a mechanical arm 105 and/or a non-mechanical tracking system 106 (e.g., an optical tracking system, an electro-magnetic tracking system), and the rollable digitizer 10.

The surgical robot 102 may include a movable base 108, a manipulator arm 110 connected to the base 108, an end-effector flange 112 located at a distal end of the manipulator arm 110, and an end-effector assembly 82 removably attached to the flange 112 by way of an end-effector mount/coupler 113. The end-effector assembly 82 holds and/or operates a cutting instrument 84 that interacts with a portion of a patient's anatomy. The base 108 includes a set of wheels 117 to maneuver the base 108, which may be fixed into position using a braking mechanism such as a hydraulic brake. The base 108 may further include an actuator 109 to adjust the height of the manipulator arm 110. The manipulator arm 110 includes various joints and links to manipulate the tool 115 in various degrees of freedom. The joints are illustratively prismatic, revolute, spherical, or a combination thereof.

The computing system 104 generally includes a planning computer 114; a device computer 116; an optional tracking computer 119 if a tracking system 106 is present; and peripheral devices. The planning computer 114, device computer 116, and tracking computer 119, may be separate entities, single units, or combinations thereof depending on the surgical system. The peripheral devices allow a user to interface with the robotic surgical system 100 and may include: one or more user-interfaces, such as a display or monitor 120; and user-input mechanisms, such as a keyboard 121, mouse 122, pendent 124, joystick 126, foot pedal 128, or the monitor 120 in some inventive embodiments may have touchscreen capabilities.

The planning computer 114 contains hardware (e.g., processors, controllers, and memory), software, data and utilities that are in some inventive embodiments dedicated to the planning of a surgical procedure, either pre-operatively or intra-operatively. This may include reading medical imaging data, segmenting imaging data, constructing three-dimensional (3D) virtual models, storing computer-aided design (CAD) files, highlighting and/or identifying bone regions for bone quality analysis, modeling the bones range-of-motion, executing finite element analysis, and generating final surgical plan data. The final surgical plan may include image data of the bones, patient data, registration data, implant position data, the location of bone regions for bone quality analysis, operational data for modifying a volume of tissue that is defined relative to the anatomy, such as a set of points in a cut-file to autonomously modify the volume of bone, a set of virtual boundaries defined to haptically constrain a tool within the defined boundaries to modify the bone, a set of planes or drill holes to drill pins in the bone, or a graphically navigated set of instructions for modifying the tissue, and combinations thereof. The data generated from the planning computer 114 may be transferred to the device computer 116 and/or tracking computer 136 through a wired or wireless connection in the operating room (OR); or transferred via a non-transient data storage medium (e.g., a compact disc (CD), a portable universal serial bus (USB) drive).

The device computer 116 in some inventive embodiments is housed in the moveable base 108 and contains hardware (e.g., controllers), software, data and utilities that are preferably dedicated to the operation of the surgical robot 102. This may include surgical device control, robotic manipulator control, the processing of kinematic and inverse kinematic data, the execution of registration algorithms, the execution of calibration routines, the execution of surgical plan data, coordinate transformation processing, providing workflow instructions to a user, utilizing position and orientation (POSE) data from the tracking system 106, and reading data received from the mechanical arm 105.

The optional tracking system 106 of the surgical system 100 may be an optical tracking system as described in U.S. Pat. No. 6,061,644. The optical tracking system includes two or more optical receivers 130 to detect the position of tracking arrays (26, 132a, 132b, 132c), where each tracking array (26, 132a, 132b, 132c) has a unique arrangement of fiducial markers 22, or a unique transmitting wavelength/frequency if the markers 22 are active LEDs. The tracking system 106 may be built into a surgical light, located on a boom, a stand 140, or built into the walls or ceilings of the OR. The tracking system computer 136 may include tracking hardware, software, data and utilities to determine the POSE of objects (e.g., bones B, rollable digitizer 10, and surgical robot 102) in a local or global coordinate frame. The POSE of the objects is collectively referred to herein as POSE data, where this POSE data may be communicated to the device computer 116 through a wired or wireless connection. Alternatively, the device computer 116 may determine the POSE data using the position of the fiducial markers detected from the optical receivers 130 directly.

The POSE data is used by the computing system 104 during the procedure to update the POSE and/or coordinate transforms of the bone B, the surgical plan, and the surgical robot 102 as the manipulator arm 110 and/or bone B move during the procedure, such that the surgical robot 102 can accurately execute the surgical plan. In another embodiment, the surgical system 100 does not include a tracking system 106, but instead employs a mechanical arm 105, and a bone fixation and monitoring system that fixes the bone directly to the surgical robot 102 and monitors bone movement as described in U.S. Pat. No. 5,086,401.

Other Embodiments

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient roadmap for implementing the exemplary embodiment or exemplary embodiments. It should be understood that various changes may be made in the function and arrangement of elements without departing from the scope as set forth in the appended claims and the legal equivalents thereof.

The invention claimed is:

1. A method of analyzing the quality of bone at one or more bone regions during an orthopedic surgical procedure to adjust a surgical plan intra-operatively or improve clinical outcomes, comprising:
    obtaining a database of audio samples correlated to a degree of bone quality;
    recording a first audio sample, with the acoustic sensor, while the cutting instrument cuts a first bone region; and
    matching the first audio sample to an audio sample in the database to analyze the bone quality of the first bone region based on the degree of bone quality correlated with the matched audio sample.

2. A system for performing the method of claim 1, comprising:
    a cutting instrument for cutting the bone;
    an acoustic sensor for sensing the first audible sample; and
    a processor for processing the first audible sample.

3. The method of claim 1 further comprising recording a second audio sample, with the acoustic sensor, while the cutting instrument cuts a second bone region.

4. The method of claim 1 further comprising transforming the first audio sample into the frequency domain to compare and analyze the first audio sample to an audio sample in the database.

5. The method of claim 4 wherein the transforming is with Fourier analysis.

6. The method of claim 1 further comprising adding additional inputs into the comparison and analysis, the additional inputs including at least one of the cutting instrument spindle speed, saw oscillating frequency, velocities of a robotic arm or surgical device while making the cuts, force data generated on the cutting instrument, historical data from previous surgical procedures, pre-operative bone quality data from the image data sets, experimental data, or combinations thereof.

7. The method of claim 1 further comprising:
    obtaining an image data set of the bone, said image data set having bone quality data associated with a plurality of bone regions; and
    planning a position of an implant relative to the bone based, in part, on the bone quality data at one or more bone regions.

8. The method of claim 7 further comprising adjusting at least one of a model, a size, or a position of an implant relative to the bone when the analyzed bone quality at the first region of the bone is substantially different from an expected bone quality as expected from the bone quality data associated with first region of the bone in the image data set.

9. The method of claim 1 further comprising providing instructions to a user, based on the analysis, to either: a) adjust at least one of a model, a size, or a position of an implant relative to the bone; b) create one or more additional cuts at one or more locations on the bone; c) augment the bone with one or more additional implant components; or d) a combination thereof.

10. The method of claim 1 further comprising creating one or more additional cuts at one or more locations on the bone when the analyzed bone quality at the first region of the bone is substantially different from an expected bone quality as expected from the bone quality data associated with the first region in the image data set.

11. The method of claim 1 further comprising augmenting the bone with one or more addition implants when the analyzed bone quality at the first region of the bone is substantially different from an expected bone quality as expected from the bone quality data associated with the first region of the bone in the image data set.

* * * * *